United States Patent [19]

Imanari et al.

[11] Patent Number: 5,155,263

[45] Date of Patent: Oct. 13, 1992

[54] PROCESS FOR PREPARING α-KETOBUTYRIC ACID

[75] Inventors: Makoto Imanari; Hiroshi Iwane; Masashi Suzuki; Naoki Suzuki, all of Ibaraki, Japan

[73] Assignee: Mitsubishi Petrochemical Co., Ltd., Tokyo, Japan

[21] Appl. No.: 767,359

[22] Filed: Sep. 30, 1991

Related U.S. Application Data

[63] Continuation of Ser. No. 359,578, Jun. 1, 1989, abandoned.

[30] Foreign Application Priority Data

Jun. 6, 1988 [JP] Japan .................. 63-138661

[51] Int. Cl.$^5$ ........................................ C07C 51/16
[52] U.S. Cl. ........................................ 562/538
[58] Field of Search ........................ 562/538

[56] References Cited

U.S. PATENT DOCUMENTS 4,620,034 10/1986 Smits .................. 562/531

FOREIGN PATENT DOCUMENTS 2527600 12/1983 France .................. 562/538
49-30315 3/1974 Japan .................. 562/538

*Primary Examiner*—Jose G. Dees
*Assistant Examiner*—Joseph M. Conrad, III
*Attorney, Agent, or Firm*—Oblon, Spivak, McClelland, Maier & Neustadt

[57] ABSTRACT

A process for preparing α-ketobutyric acid comprising contacting 1,2-butanediol with molecular oxygen in the presence of a platinum catalyst is disclosed. The process produces α-ketobutyric acid in high yield at low cost.

7 Claims, No Drawings

PROCESS FOR PREPARING α-KETOBUTYRIC ACID

This application is a continuation of application Ser. No. 07/359,578, filed on Jun. 1, 1989, now abandoned.

FIELD OF THE INVENTION

This invention relates to a process for preparing α-ketobutyric acid by oxidation of 1,2-butanediol with molecular oxygen.

α-Ketobutyric acid is an important intermediate in the biosynthesis of, for example, L-isoleucine from L-threonine and is useful as a good starting material for amino acid syntheses.

BACKGROUND OF THE INVENTION

Known processes for synthesizing α-ketobutyric acid include hydrolysis of α-ketobutyronitrile, hydrolysis of α-methoxycrotonic acid obtainable from crotonic acid, and reaction between diethyl oxalate and triethylaluminum. These conventional processes, however, are not regarded industrially practical because of expensiveness of the starting materials.

SUMMARY OF THE INVENTION

One object of this invention is to provide a process for preparing α-ketobutyric acid in high yield at low cost by oxidation of inexpensive 1,2-butanediol.

The present invention relates to a process for preparing α-ketobutyric acid which comprises oxidizing 1,2-butanediol with molecular oxygen in the presence of a platinum catalyst.

DETAILED DESCRIPTION OF THE INVENTION

The oxidation reaction according to the present invention is carried out in a liquid phase and advantageously in an aqueous solution. The 1,2-butanediol aqueous solution to be used usually has a concentration of from 0.5 to 30% by weight, preferably from 1 to 15% by weight.

The reaction is performed in the presence of a platinum catalyst. The platinum catalyst is composed of platinum either alone or in combination with at least one metallic component selected from the group consisting of lead, thallium, cadmium, and indium, each of which being in the form either of an element or of a compound thereof. The catalyst composed of both platinum and other element achieves higher yields of α-ketobutyric acid than the catalyst solely composed of platinum. The catalyst component is usually used as being supported on an appropriate carrier, such as activated carbon, alumina, and magnesia, with activated carbon being widely employed. The amount of the platinum component to be supported on the carrier ranges from 0.5 to 15%, preferably from 1 to 10%, by weight, while that of other element component(s) ranges from 0 to 20%, preferably from 1 to 10%, by weight.

The catalyst-on-carrier, for example, a platinum-lead catalyst can be prepared by impregnating a mixed aqueous solution of chloroplatinic acid and lead acetate into activated carbon, drying, washing with water, suspending the impregnated activated carbon in water, and reducing with formalin, hydrazine or hydrogen. It may also be obtained by impregnating a water-soluble lead compound (e.g., lead nitrate) into a commercially available platinum-on-carrier catalyst. Platinum catalysts containing other metallic elements than lead can be obtained in a similar manner.

The amount of the catalyst to be used is not particularly limited, but the total content of platinum and other elements is usually in a range of from 0.1 to 5% by weight based on 1,2-butanediol. The spent catalyst can be collected by filtration for reuse.

The molecular oxygen which can be used in this invention includes not only pure oxygen but mixed oxygen gases containing an inert gas (e.g., nitrogen) such as air. The reaction pressure usually ranges from atmospheric pressure to 20 kg/cm$^2$, preferably from atmospheric pressure to 4 kg/cm$^2$.

It is recommended to maintain the reaction system neutral or basic since the reaction rate becomes low in an acidic condition. Maintenance of the reaction system at a neutral or basic pH value, an alkaline substance is added to the reaction mixture. The alkaline substance to be used includes alkali metal hydroxides, e.g., sodium hydroxide, alkali metal carbonates or bicarbonates, alkaline earth metal hydroxides, and ammonium hydroxide.

The alkaline substance may be added all at once at the initial stage of the reaction, but it is preferably added in divided portions synchronously with the reaction progress so as to maintain the pH of the reaction mixture between 7 and 11 during the reaction.

The reaction is conducted at a temperature of from 20° to 100° C., preferably from 40° to 80° C. The reaction time usually ranges from 2 to 10 hours, though varying depending on the amount of the catalyst and the reaction temperature.

The present invention is now illustrated in greater detail by way of the following Examples, but it should be understood that the present invention is not deemed to be limited thereto. In these examples, all the percents are by weight unless otherwise indicated.

EXAMPLE 1

In 200 ml-volume flask equipped with a stirrer, a condenser, an inlet for oxygen feed, an inlet for alkali feed, and electrodes for pH measurement were charged 4.50 g of 1,2-butanediol, 151 g of water, and 1.80 g of an activated carbon powder having carried thereon 5% of platinum. The reaction mixture was stirred at 70° C. for 7.5 hours while feeding oxygen at a rate fixed at about 12Nl/hr. During the reaction, a 10% aqueous solution of sodium hydroxide was added dropwise to the reaction mixture so that the consumed sodium hydroxide might be always made up and the reaction mixture be kept at a pH between 7 and 9.

The reaction mixture was analyzed by high performance liquid chromatography. As a result, it was revealed that 1.58 g (yield: 25.5%) of sodium α-ketobutyrate was produced.

EXAMPLES 2 TO 5

In the same reaction vessel as used in Example 1 were charged 4.50 g of 1,2-butanediol, 151 g of water, and an activated carbon powder having carried thereon 5% of platinum and 5% of other element shown in Table 1 in an amount shown in Table 1. The reaction mixture was allowed to react and analyzed in the same manner as in Example 1. The results obtained are shown in Table 1.

TABLE 1

| Example No | Element | Amount of Catalyst (g) | Water content of Catalyst (%) | Reaction Time (hr) | Yield (%) |
|---|---|---|---|---|---|
| 2 | Pb | 3.07 | 41.4 | 7.5 | 87.1 |
| 3 | Tl | 2.17 | 17.0 | 6.0 | 72.4 |
| 4 | Cd | 2.60 | 30.7 | 7.0 | 51.6 |
| 5 | In | 1.89 | 5.0 | 5.3 | 31.5 |

EXAMPLE 6

Reaction was carried out in the same manner as in Example 2, except for using the catalyst having been used in Example 2 and collected by filtration and conducting the reaction for 5.0 hours. As a result of analysis of the reaction mixture, the yield of sodium α-ketobutyrate was found to be 81.6%, indicating no reduction of the catalytic activity even after repeated use.

EXAMPLE 7

In the same reaction vessel as used in Example 1 were charged 4.50 g of 1,2-butanediol, 169 g of water, 4.35 g of an activated carbon powder having carried thereon 5% of platinum and 5% of lead (water content: 58.6%), and 2.01 g of sodium hydroxide. The reaction was effected at 70° C. for 7.5 hours while maintaining the oxygen feed at about 12Nl/hr. As a result of analysis of the reaction mixture, the yield of sodium α-ketobutyrate was found to be 37.3%.

While the invention has been described in detail and with reference to specific embodiments thereof, it will be apparent to one skilled in the art that various changes and modifications can be made therein without departing from the spirit and scope thereof.

What is claimed is:

1. A process for preparing α-ketobutyric acid comprising contacting 1,2-butanediol with molecular oxygen in the presence of a platinum catalyst containing at least one metallic component selected from the group consisting of lead, thallium, and cadmium.

2. A process as claimed in claim 1, wherein said platinum catalyst is a catalyst-on-carrier containing from 0.5 to 15% by weight of platinum and up to 20% by weight of the other metallic element or elements based on the carrier.

3. A process as claimed in claim 1, wherein said platinum catalyst is a catalyst-on-carrier containing from 1 to 10% by weight of platinum and from 1 to 10% by weight of the other metallic component or components based on the carrier.

4. A process as claimed in claim 1, wherein said platinum catalyst is present in an amount of from 0.1 to 5% by weight based on 1,2-butanediol.

5. A process as claimed in claim 1, wherein the 1,2-butanediol is in an aqueous solution at a concentration of from 0.5 to 30% by weight.

6. A process as claimed in claim 1, wherein the 1,2-butanediol is in an aqueous solution at a concentration of from 1 to 15% by weight.

7. A process as claimed in claim 1, wherein said contacting is at a pH between 7 and 11.

* * * * *